(12) United States Patent
Mareiro et al.

(10) Patent No.: US 6,258,099 B1
(45) Date of Patent: Jul. 10, 2001

(54) STENT SECURITY BALLOON/BALLOON CATHETER

(75) Inventors: Wayne Mareiro, Pepperell; Robert Estes, Danvers; Ralph J. Barry, Jr., Hudson, all of MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/283,375

(22) Filed: Mar. 31, 1999

(51) Int. Cl.[7] ........................................................ A61F 11/00
(52) U.S. Cl. ........................ 606/108; 604/96.01; 606/192
(58) Field of Search ........................................ 606/108, 192, 606/194, 195; 604/104, 915, 916, 96.01, 97.2, 103.07, 103.08

(56) References Cited

U.S. PATENT DOCUMENTS

| | | |
|---|---|---|
| 4,694,827 | 9/1987 | Weiner et al. . |
| 4,927,412 | 5/1990 | Menasche . |
| 5,074,845 | 12/1991 | Miraki et al. . |
| 5,163,989 | 11/1992 | Campbell et al. . |
| 5,250,070 | 10/1993 | Parodi . |
| 5,423,745 | 6/1995 | Todd et al. . |
| 5,456,666 | 10/1995 | Campbell et al. . |
| 5,478,319 | 12/1995 | Campbell et al. . |
| 5,487,730 | 1/1996 | Marcadis et al. . |
| 5,503,631 | 4/1996 | Onishi et al. . |
| 5,545,132 | 8/1996 | Fagan et al. . |
| 5,653,690 | 8/1997 | Booth et al. ........................... 604/96 |
| 5,693,014 | 12/1997 | Abele et al. . |
| 5,746,745 | 5/1998 | Abele et al. . |
| 5,772,669 | 6/1998 | Vrba . |
| 5,807,327 | 9/1998 | Green et al. . |
| 5,826,588 | 10/1998 | Forman . |
| 5,836,965 | 11/1998 | Jendersee et al. . |
| 5,868,703 | * 2/1999 | Bertolero et al. ..................... 604/102 |
| 5,935,135 | * 8/1999 | Bramfitt et al. ...................... 606/108 |
| 5,976,155 | * 11/1999 | Foreman et al. ..................... 606/108 |
| 6,027,510 | * 2/2000 | Alt ...................................... 606/108 |

FOREIGN PATENT DOCUMENTS

| | | |
|---|---|---|
| 0 834 293 A1 | 4/1998 | (EP) . |
| 2 753 907 A1 | 4/1998 | (FR) . |
| 87/00442 | 1/1987 | (WO) . |
| 94/23787 | 10/1994 | (WO) . |
| 98/07390 | 2/1998 | (WO) . |

* cited by examiner

*Primary Examiner*—Manuel Mendez
(74) *Attorney, Agent, or Firm*—Vidas, Arrett & Steinkraus

(57) ABSTRACT

A medical balloon is constructed with protrusions thereon to prevent unwanted movement of an expandable, implantable medical device such as a stent during delivery and deployment. At least some of the protrusions are underlying the expandable, implantable medical device to grip the expandable, implantable medical device.

18 Claims, 5 Drawing Sheets

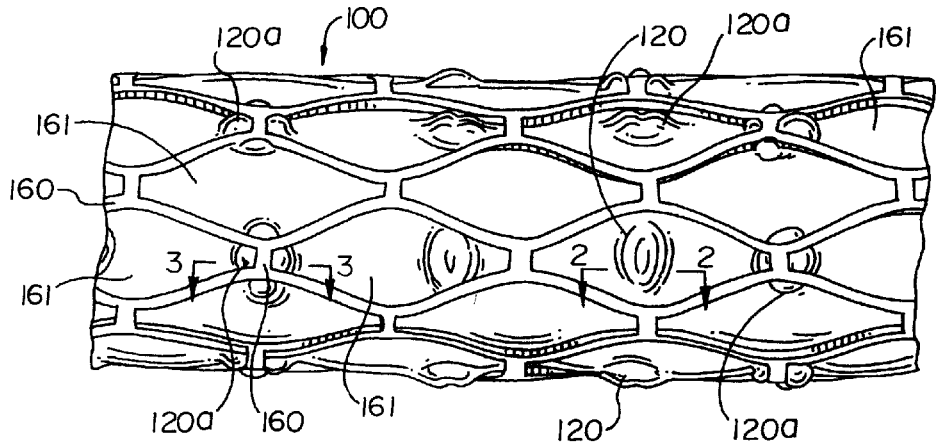
Fig. 1
Fig. 2
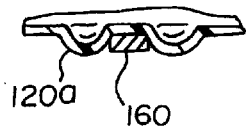
Fig. 3a
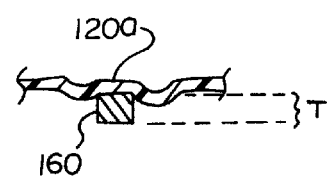
Fig. 3b
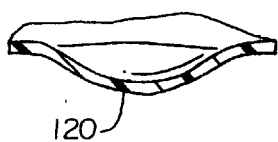
Fig. 4a
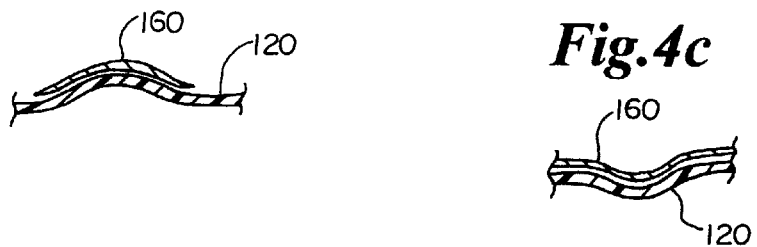
Fig. 4b
Fig. 4c

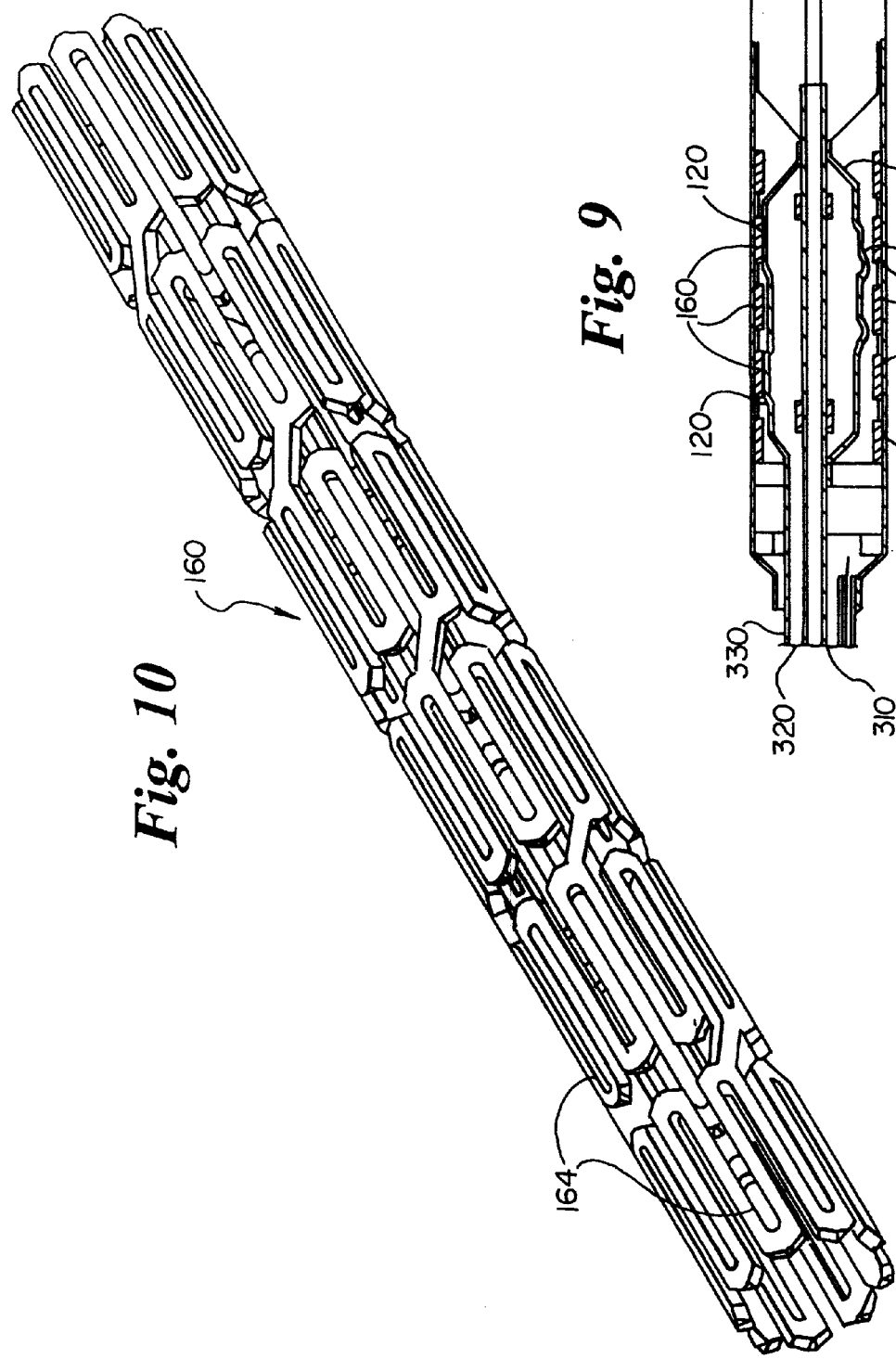

STENT SECURITY BALLOON/BALLOON CATHETER

BACKGROUND OF THE INVENTION

This invention relates to a medical balloon for use in expanding or seating a medical device such as a stent at a desired bodily location. More specifically, this invention relates to a balloon having protrusions thereon which are constructed and arranged to prevent unwanted movement of an expandable medical device such as a stent, stent-graft, graft or vena cava filter mounted thereon.

Expandable, implantable medical devices such as stents are utilized in a number of medical procedures and situations as are stent delivery assemblies. As such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Self-expanding, inflation assisted expandable and inflation expandable stents are well known and widely available in a variety of designs and configurations. Inflation expandable and inflation assisted expandable stents are expanded via outward radial pressure such as that provided by a balloon disposed underneath the stent during inflation of the balloon.

In using such stents and other expandable, implantable medical devices, it is necessary to position the expandable, implantable medical device in a precise location within a bodily lumen. This goal is rendered more difficult because slippage may occur during insertion of the expandable, implantable medical device through a guide catheter or during deployment of the expandable, implantable medical device. To facilitate the proper positioning of an expandable, implantable medical device, it is desirable to prevent any unwanted relative movement between any of the expandable, implantable medical device, the balloon, the catheter and the interior of the vessel.

One approach to limiting slippage in a catheter assembly involves providing a balloon whose body has a lubricating portion and a non-lubricating portion. This approach is directed in particular to the so-called 'watermelon seed' problem wherein a balloon which is too lubricious shoots forward on inflation.

Approaches to reducing slippage of the balloon relative to the vessel involve the use of a balloon with spikes, felt, or other shaped surface thereon which frictionally engages the interior of the vessel.

These approaches address balloon slippage in a lesion. They do not address the problem of slippage of an expandable, implantable medical device relative to a balloon.

The issue of slippage of an expandable, implantable medical device relative to a balloon has been dealt with in several different ways including by varying the coefficient of friction of the exposed portion of a balloon between the uninflated and inflated states of the balloon. Another approach involves providing a balloon with enlarged ends and a middle section of reduced diameter to retain a stent. Yet another approach involves encapsulated a stent with a balloon. Other approaches are nonballoon based, providing stent retention devices that extends from the catheter and engage the stent.

Patents, publications and applications of interest include U.S. Pat. No. 5,503,631 to Onishi, U.S. Pat. No. 5,545,132 to Fagan, U.S. Pat. No. 5,746,745 to Abele et al., U.S. Pat. No. 5,423,745 to Todd et al., U.S. Pat. No. 5,487,730 to Marcadis et al., U.S. Pat. No. 5,250,070 to Parodi, U.S. Pat. No. 4,927,412 to Menasche, U.S. Pat. No. 5,836,965 to Jendersee et al., WO 94/23787 and copending and commonly assigned U.S. patent application Ser. No. 09/141209.

It is a goal of the present invention to provide a medical device delivery system with improved medical device deployment accuracy which prevents slippage of the expandable, implantable medical device during delivery of the device to a desired bodily location and during deployment of the device to facilitate the positioning of the expandable, implantable medical device. In particular, it is a goal of the present invention to provide a stent delivery system having a balloon with protrusions extending therefrom to prevent the stent from substantially moving longitudinally relative to the balloon until the stent has been deployed.

All US patents and all other published documents mentioned anywhere in this application are incorporated herein by reference in their entirety.

BRIEF SUMMARY OF THE INVENTION

The present invention provides a medical balloon having one or more protrusions extending from the surface which engage an expandable, implantable medical device mounted thereon. The protrusions may extend outward and/or inward from the surface of the balloon. In one embodiment of the invention, one or more protrusions extend inwards and one or more protrusions extend outwards. Upon inflation of the balloon, the inwardly extending protrusions may invert so as to extend outward.

The medical balloons disclosed herein find particular utility in the deployment of expandable, implantable medical devices including stents, grafts, stent grafts and vena cava filters.

A variety of shapes is contemplated for the protrusions including cylindrical, pyramidal, conical and tubular.

In one embodiment of the invention, the at least one protrusion extends from the body portion of the balloon.

The invention also contemplates a medical device delivery catheter having a balloon mounted thereon with protrusions extending from the balloon to aid in retaining an expandable, implantable medical device on the balloon.

The invention further provides a method of delivering a medical device to a bodily location. In accordance with the inventive method, a medical device delivery apparatus including an inventive balloon and an expandable, implantable medical device disposed about the balloon is provided. At least a portion of the apparatus is inserted in a bodily vessel including the balloon and expandable, implantable medical device and advanced to a desired bodily location where the balloon is inflated to expand the expandable, implantable medical device. The balloon is then at least partially deflated and the medical device delivery apparatus withdrawn from the body.

BRIEF DESCRIPTION OF THE SEVERAL VIEWS OF THE DRAWING(S)

FIG. 1 shows a fragmentary side elevational view of an inventive medical balloon with a stent mounted thereon;

FIG. 2 is a partial cross-sectional view of FIG. 1 taken along lines 2—2;

FIG. 3a is a partial cross-sectional view of FIG. 1 taken along lines 3—3;

FIG. 3b is a partial cross-sectional view similar to that of FIG. 3a;

FIG. 4a is a partial cross-sectional view similar to that of FIG. 2, of an outward extending protrusion;

FIGS. 4b and 4c are partial cross-sectional views showing a portion of a stent conformed to an outward extending protrusion (FIG. 4b) and to an inward extending protrusion (FIG. 4c);

FIG. 9 shows an expanded view of the distal end of the catheter of FIG. 8; and

FIG. 10 shows a stent suitable for use with the present invention.

DETAILED DESCRIPTION OF THE INVENTION

Figure 5A:
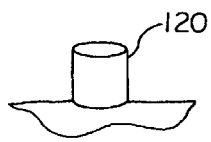
FIG. 5a shows a substantially cylindrical protrusion.

While this invention may be embodied in many different forms, there are described in detail herein specific preferred embodiments of the invention. This description is an exemplification of the principles of the invention and is not intended to limit the invention to the particular embodiments illustrated.

The inventive balloons shown in fragmentary view generally at 100 in FIG. 1 have protrusions 120 extending from the balloon. The protrusions may be disposed regularly or irregularly about the body portion of balloon 100 or may be disposed at either the proximal or distal end of the balloon. Moreover, the protrusions may be disposed irregularly about the body portion of balloon 100 with respect to openings 161 of stent 160 as shown in FIG. 1. Stent 160, shown mounted on balloon 100, is engaged by at least some of the protrusions 120a. Protrusions 120a extend between adjacent openings 161 in stent 160.

The invention also contemplates protrusions which are disposed regularly about the body portion of a balloon with respect to the openings of the stent mounted thereon. The protrusions may also be disposed at either the proximal or distal end of the balloon.

Protrusions 120 on balloon 100, as shown in FIG. 1, are inwardly extending protrusions that, as a result of partial inflation of the balloon, partially extend outward. A view of one such protrusion 120 is shown in FIG. 2. Protrusion 120 is seen to have a 'W' shape in cross section as it has not fully inverted.

At least some of the protrusion engage portions of the stent. FIG. 3a shows a protrusion 120a engaging a portion of stent 160. In FIG. 3a, protrusion 120a extends upwards to the total thickness of the stent. Preferably, the protrusions will only extend upward to a portion of the stent thickness. FIG. 3b shows a protrusion 120a which only engages a stent 160 to a portion of the thickness T of the stent. Desirably, the protrusions will only extend around the stent struts or the portion of the stent which they grip to a distance of about 30 percent to 50 percent of the thickness of the stent or stent strut. The exact height of the protrusion will depend on the balloon materials and balloon wall thickness. Typically, the inventive balloons will have protrusions extending out about 0.001 inches to about 0.003 inches. These balloons will typically be used to deliver stents with thicknesses of about 0.003 inches to about 0.007 inches. The diameter of the protrusions is desirably about 0.01 inches to about 0.06 inches across. More desirably, the diameter of the protrusions is about 0.015 inches to about 0.03 inches across. Most desirably, the diameter of the protrusions will be about 0.03 inches across.

The inventive balloons may also be made with protrusions which extend outward in both the uninflated state and in the inflated state. A cross-sectional view of an outward extending protrusion is shown at 120 in FIG. 4a. Such a balloon will resemble that shown in FIG. 1 with the protrusions 120 extending fully outward.

In the case of balloon expandable stents which are typically crimped to the balloon, the stent will desirably locally confirm somewhat to the shape of the protrusions to further improve stent retention. Thus, in the case of outward extending protrusions, as shown in FIG. 4b, the portion of the stent 160 in contact with protrusion 120 will bend slightly over the protrusion. Where the protrusions extend inward, as shown in FIG. 4c, the portion of stent 160 over protrusion 120 will extend into the protrusion on crimping the stent to the balloon. The conformed stent will lie atop a protrusion.

The exact number of protrusions may be chosen to facilitate retention of the expandable, implantable medical device prior to deployment thereof while not significantly weakening the balloon. While increasing the number of protrusions facilitates retention of the expandable, implantable medical device, too many protrusions hampers release of the medical device and also weaken the balloon.

Various regular or irregular spatial arrangements of the protrusions may be employed in the practice of the present invention. Regardless of the arrangement of the protrusions on the balloon, the position of the protrusions need not be correlated with the struts or the openings between the struts of the stent as long as some of the protrusions engage some of the stent struts. In a desired embodiment, some of the protrusions will engage the stent while some of the protrusions will fall in the openings between struts and will not engage the stent.

Figure 5B:
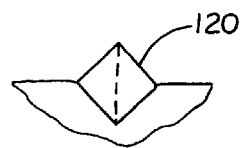
FIG. 5b shows a substantially pyramidal protrusion.
Figure 5C:
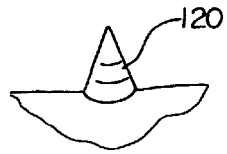
FIG. 5c shows a substantially conical protrusion.
Figure 5D:
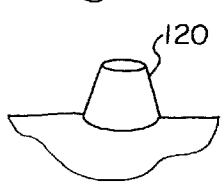
FIG. 5d shows a substantially frustoconical protrusion.
Figure 5E:
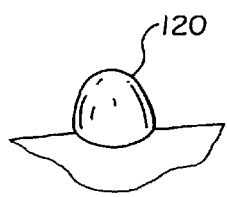
FIG. 5e shows a protrusion with a rounded end.
Figure 5F:
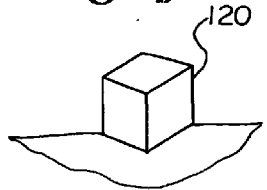
FIG. 5f shows a polygonal protrusion with a polygonal shaped end.

The shape of the protrusions can also affect the retention characteristics of the balloon. In addition to the protrusions shown in the above figures, the invention also contemplates other shaped protrusions including cylindrical protrusions 120 as shown in FIG. 5a, substantially pyramidal protrusions 120 as shown in FIG. 5b, substantially conical protrusions 120 as shown in FIG. 5c, substantially frustoconical protrusions 120 as shown in FIG. 5d, protrusions which terminate in a rounded end 120 as shown in FIG. 5e and polygonal protrusions 120 which terminate in polygons such as squares, shown in FIG. 5f. Polygonal protrusions which terminate in other shaped polygons such as triangles, pentagons and hexagons are also contemplated. Other shaped protrusions may be employed as well.

More generally, any other shaped protrusions which will grip an expandable, implantable medical device and prevent unwanted motion of the device may be used.

Figure 5G:
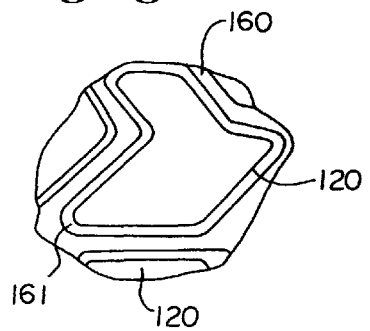
FIG. 5g is a simplified fragmentary diagram showing a stent and a balloon protrusion extending between the struts of a stent.

The invention also contemplates the possibility of matching the balloon protrusion(s), including its shape, size and orientation, to the shape and size of the openings in a stent or other medical device. FIG. 5g is a simplified fragmentary diagram of a balloon with protrusions 120 that are shaped to match the openings 161 of stent 160.

Figure 6A:
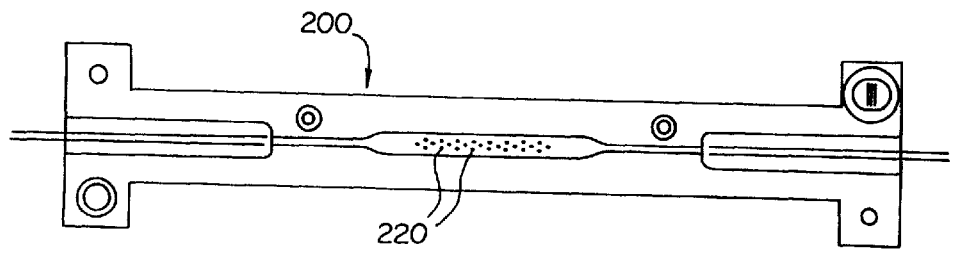
FIG. 6a shows a side elevational view of a balloon mold.
Figure 6B:
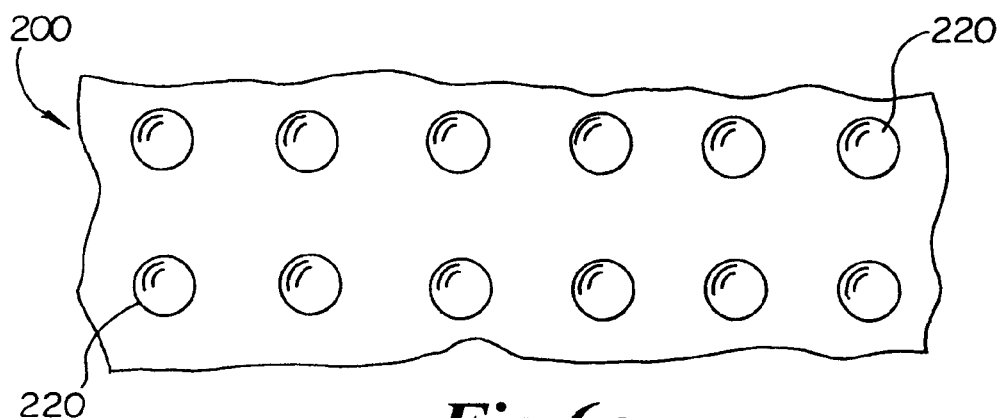
FIG. 6b shows a fragmentary view of the interior of a balloon mold with bumps thereon.

The inventive balloons may be made by incorporating the protrusions into the balloon via a mold heat set process using molds such as that shown generally at 200 in FIG. 6a. Mold 200 has a plurality of outward extending protrusions 220 thereon, as shown in FIG. 6b. In molding a balloon, outward extending protrusions 220 on mold 200 produce inward extending protrusions in a balloon.

Figure 6C:
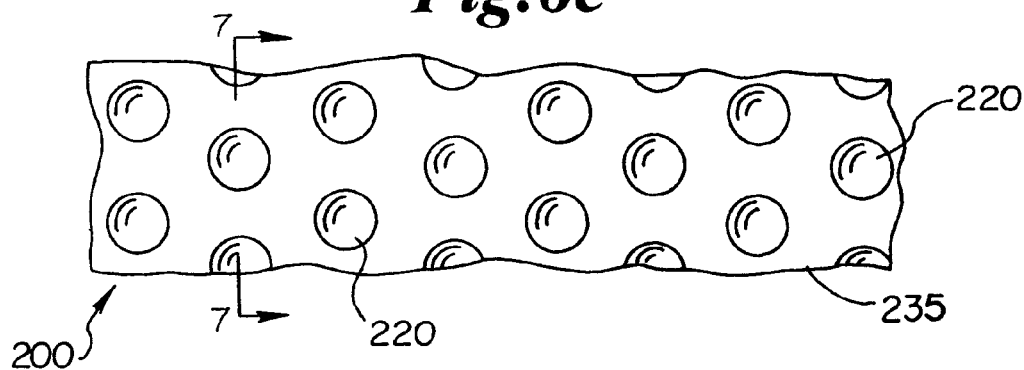
FIG. 6c shows a fragmentary view of the interior of a balloon mold with another arrangement of bumps thereon.
Figure 7:
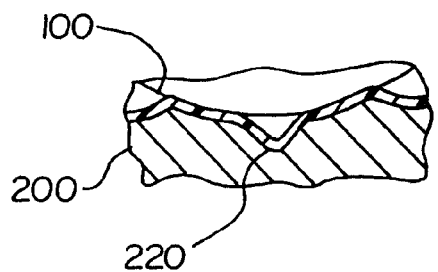
FIG. 7 shows a partial cross-section of FIG. 6c taken along lines 7—7.

Another such mold is shown generally at 200 in FIG. 6c. Mold 200 has a plurality of inward extending protrusions 220. FIG. 7, a partial cross-sectional view of the mold of FIG. 6c taken along lines 7—7, illustrates the inward protrusions in the mold. Mold 200 of FIG. 6c will produce a balloon with outward extending protrusions.

The molds of FIGS. 6b and 6c differ not only in the direction of the protrusions, but also in the arrangement of the protrusions. They further differ in that mold 200 of FIG. 6c has a textured interior surface 235. This optional texturing is transferred to the balloon on molding the balloon.

Molds having both inwardly and outwardly extending protrusions may also be used as may molds having other shaped protrusions, as discussed above.

Prior to molding, the balloon may be pre-blown using a standard commercial process. Once in the mold, the balloon preform is heated to a desired temperature to incorporate the protrusions and any texturing into the balloon. The particular temperature will depend on the choice of balloon material. During the molding, the balloons are blown. One suitable molding process is set out in greater detail in U.S. Pat. Nos. 5,456,666 and 5,478,319.

Other techniques for forming protrusions on the surface of the balloon include selective removal of materials from a balloon preform or a balloon such as laser ablation, etching, grinding or other techniques as disclosed in U.S. Pat. No. 5,826,588 to Forman.

The protrusion(s) disclosed herein may be provided on any suitable balloon intended for use in delivering an expandable, implantable medical device mounted thereabout. As such, the physical characteristics of the balloon may vary. The balloon may be compliant or non-compliant or may be compliant in-part and noncompliant in part. The wall thickness of the balloon may be constant over the entire balloon or may vary in different parts of the balloon. The balloon may be formed of one layer of material or may consist of a plurality of layers. The balloon may be formed of a single piece of balloon material or may be formed of several pieces joined together along the length of the balloon.

The inventive balloons may be made from any balloon material known in the art including polyethylene, polyethylene terephthalate (PET), Arnitel, Hytrel, polyetherether ketone (PEEK), Pebax, Teflon as well as other polyolefins. Other thermoplastic elastomers may be used as well. Where the balloon is made of a noncompliant material such as PET, upon inflation of the balloon, the protrusions extend further outward until the non-compliant region of the balloon is reached. At that point, the protrusions cease to grow in height and flatten out instead with the diameter of the protrusion increasing. More generally, any thermoplastic elastomer treatable by a blow molding process may be used.

Figure 8:
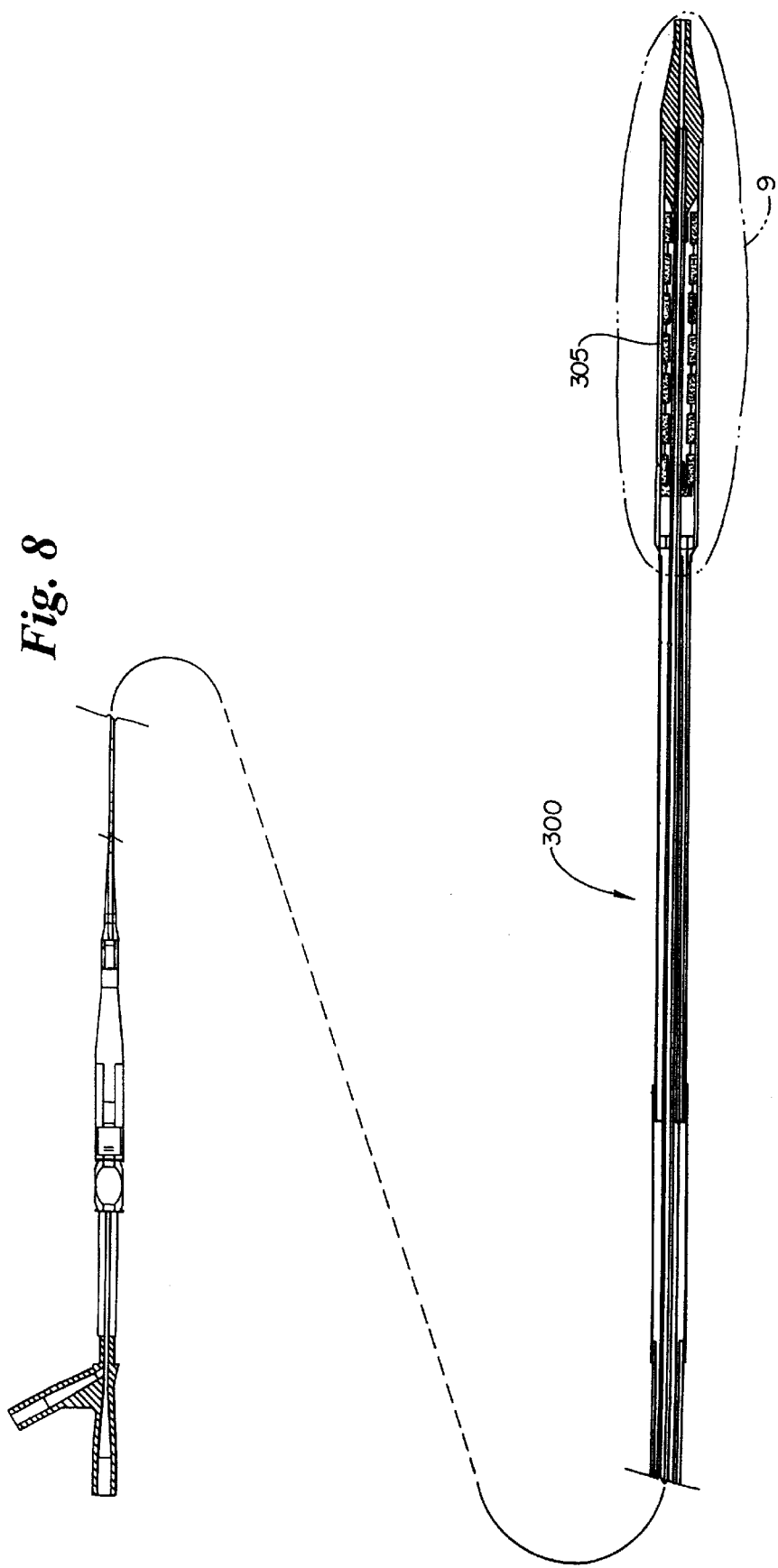
FIG. 8 shows a stent delivery catheter.

The invention is also directed to a catheter having an inventive balloon mounted thereon. Any suitable balloon-based stent delivery catheter may be used. One such catheter is shown generally at 300 in FIG. 8. Distal end 305 of catheter 300 may be modified to accommodate a balloon as shown in FIG. 9. An inventive balloon 100 is disposed about an inner tube 310. The proximal end of balloon 100 is mounted to tube 330. The distal end of balloon 100 is mounted to inner tube 310. Disposed about balloon 100 is a self-expanding stent 160 which is retained in its place by retractable sheath 315. Balloon 100 is supplied with an inflation fluid by inflation lumen 320. Inflation lumen 320 is the space between tube 310 and tube 330. The invention also contemplates the possibility of a separate tube serving as an inflation lumen. The device of FIG. 8 is described in greater detail in U.S. Pat. No. 5,772,669 to Vrba.

Other suitable catheters for use in the present invention include those disclosed in WO 98/07390.

In addition to the over-the-wire catheter shown in FIGS. 8 and 9, the invention may be practiced with any other suitable catheter including rapid-exchange catheters and fixed wire catheters. The exact configuration of the delivery apparatus will depend on what other functions are desired.

The device of FIGS. 8 and 9 is shown with a self-expanding stent. Balloon expandable stents may also be used. Those of ordinary skill in the art will recognize any modifications necessary to the stent delivery catheter of FIGS. 8 and 9 to accommodate balloon expandable stents, stent-grafts, grafts and vena cava filters. Any other suitable device having a balloon thereon for delivery of any of the above expandable, implantable medical devices may also be used.

A suitable stent for use with the inventive balloons is shown at 160 in FIG. 10 for illustrative purposes. Stent 160 is formed of a plurality of interconnected struts 164. Stents with other designs may also be used in conjunction with the inventive balloons.

In another aspect, the invention is directed to methods of using the inventive medical balloon and in particular to a method of delivering an expandable, implantable medical device such as a stent to a bodily location using the inventive balloon. A medical device delivery apparatus comprising a balloon mounted on a tube is provided. The balloon has protrusions thereon sized to grip the expandable, implantable medical device disposed about the balloon. An inflation lumen is provided to supply inflation fluid to the balloon. At least a portion of the apparatus, including the balloon and expandable, implantable medical device, is inserted in a bodily vessel and advanced to a desired bodily location. The balloon is inflated to expand and/or seat and/or deploy the expandable, implantable medical device. The balloon is then at least partially deflated such that it no longer engages the expandable, implantable medical device. The expandable, implantable medical device is deployed and the apparatus withdrawn from the body.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodi-

What is claimed is:

1. A medical balloon with an expandable, implantable medical device mounted thereon, the expandable implantable medical device having an inner surface, an outer surface and a plurality of side surfaces extending between the inner surface and the outer surface, the medical balloon having an outer surface, the outer surface of the medical balloon facing the inner surface of the expandable implantable medical device, the outer surface of the medical balloon having a plurality of protrusions thereon, at least some of the protrusions at least partially underlying the expandable, implantable medical device and extending part of the way up at least one side surface of the expandable, implantable medical device to releasably engage the expandable, implantable medical device on the side surface.

2. The medical balloon of claim 1 wherein the protrusions extend outward from the balloon.

3. The medical balloon of claim 1 wherein the expandable, implantable medical device is a stent releasably engaged to the medical balloon, the protrusions releasably engaging the stent on a plurality of side surfaces.

4. A medical balloon having an outer surface and further comprising a stent releasably engaged on the outer surface of the medical balloon, the stent having openings therethrough, the outer surface of the medical balloon having a plurality of protrusions thereon, at least some of the protrusions partially extending through the openings in the stent to releasably engage the stent, wherein the protrusions are only partially conformed to the shape of the stent.

5. The medical balloon of claim 4 wherein at least some of the protrusions extend inward.

6. The medical balloon of claim 5 wherein the inwardly extending protrusions extend outward after the balloon has been inflated.

7. The medical balloon of claim 1 made of a compliant balloon material.

8. The medical balloon of claim 1 made of a non-compliant balloon material.

9. The medical balloon of claim 1 wherein the protrusions on the balloon are selected from the group consisting of substantially cylindrical, substantially frustoconical, substantially conical, substantially pyramidal and substantially polygonal protrusions.

10. The medical balloon of claim 1 comprising a proximal cone portion, a distal cone portion and a body portion disposed between the proximal and distal cone portions, wherein the protrusions are regularly spaced about the body portion of the balloon.

11. The medical balloon of claim 1 wherein the expandable, implantable medical device is a stent.

12. The medical balloon of claim 11 wherein the protrusions extend through the stent to from about 30% to about 50% of the thickness of the stent.

13. The medical balloon of claim 1 wherein the expandable medical device is a stent formed of a plurality of interconnected struts having openings therebetween and the protrusions are irregularly distributed about the balloon relative to the openings in the stent.

14. The medical balloon of claim 1 wherein the expandable medical device is a stent formed of a plurality of interconnected struts having openings therebetween and some of the protrusions engage the stent and some of the protrusions do not engage the stent.

15. The medical balloon of claim 1 wherein the expandable medical device is a stent formed of a plurality of interconnected struts having openings therebetween and some of the protrusions extend between adjacent openings in the stent.

16. A medical device delivery apparatus comprising a tube with the balloon of claim 1 mounted thereon and an inflation lumen in fluid communication with the balloon.

17. A method of delivering an expandable, implantable medical device to a bodily location comprising the steps of:
   i) providing a medical device delivery apparatus comprising
      a balloon mounted on a tube, the balloon having protrusions thereon, including inwardly directed protrusions which extend outward upon inflating the balloon.
      an inflation lumen capable of fluid communication with the balloon,
      an expandable, implantable medical device disposed about the balloon, at least some of the protrusions on the balloon underlying the expandable, implantable medical device to releasably engage the expandable, implantable medical device;
   ii) inserting at least a portion of the apparatus including the balloon and the expandable, implantable medical device into a bodily vessel;
   iii) advancing the expandable, implantable medical device and balloon to a desired bodily location;
   iv) inflating the balloon to expand the expandable implantable medical device;
   v) at least partially deflating the balloon such that the medical balloon no longer engages the expandable, implantable medical device;
   vi) withdrawing the apparatus from the body, the expandable, implantable medical device remaining in the body.

18. The method of claim 17 wherein the expandable, implantable medical device is a stent.

* * * * *